United States Patent
Pacheco et al.

(10) Patent No.: US 8,039,678 B2
(45) Date of Patent: *Oct. 18, 2011

(54) PROCESS FOR THE PREPARATION OF CHLOROMETHYL 2,2,2-TRIFLUORO-1-(TRIFLUOROMETHYL) ETHYL ETHER

(75) Inventors: Ogari Pacheco, Itapira (BR); Antonio Carlos Teixeira, Itapira (BR); Edson Luiz Lima, Itapira (BR); Maria Alice Böckelmann, Itapira (BR)

(73) Assignee: Cristalia Produtos Quimicos Farmaceuticos Ltda., Itapira (BR)

( * ) Notice: Subject to any disclaimer, the term of this patent is extended or adjusted under 35 U.S.C. 154(b) by 196 days.

This patent is subject to a terminal disclaimer.

(21) Appl. No.: 12/443,438

(22) PCT Filed: Sep. 29, 2006

(86) PCT No.: PCT/BR2006/000197
§ 371 (c)(1),
(2), (4) Date: May 12, 2009

(87) PCT Pub. No.: WO2008/037039
PCT Pub. Date: Apr. 3, 2008

(65) Prior Publication Data
US 2010/0004490 A1    Jan. 7, 2010

(51) Int. Cl.
*C07C 41/06* (2006.01)
(52) U.S. Cl. .......... 568/682; 568/681; 568/683
(58) Field of Classification Search .......... None
See application file for complete search history.

(56) References Cited

U.S. PATENT DOCUMENTS

| 4,225,677 A | 9/1980 | Boutier et al. |
| 5,811,596 A | 9/1998 | Kawai et al. |
| 6,100,434 A * | 8/2000 | Bieniarz et al. ............... 568/683 |

* cited by examiner

*Primary Examiner* — Rosalynd Keys
(74) *Attorney, Agent, or Firm* — Birch, Stewart, Kolasch & Birch, LLP

(57) ABSTRACT

The present invention refers to a process for the preparation of chloromethyl 2,2,2-trifluoro-1-(trifluoromethyl) ethyl ether (sevochlorane), which consists of reacting hexafluoroisopropanol with: a formaldehyde equivalent selected between paraformaldehyde or 1,3,5-trioxane, a chlorinating agent selected from the group consisting of oxalyl chloride, phosphorus trichloride, phosphorus pentachloride, phosphorus oxychloride, sulfuryl chloride and thionyl chloride, and a strong acid selected from the group consisting of concentrated or fuming sulfuric acid. Said process provides sevochlorane in high purity and yield, which can be converted to sevoflurane by known means.

24 Claims, No Drawings

PROCESS FOR THE PREPARATION OF CHLOROMETHYL 2,2,2-TRIFLUORO-1-(TRIFLUOROMETHYL) ETHYL ETHER

This Application is the National Phase Under 35 U.S.C. §371 of PCT International Application No. PCT/BR2006/000197 which has an International filing date of Sep. 29, 2009. The entire contents of all applications listed above are hereby incorporated by reference.

The present invention refers to the field of inhalation anesthetics. In particular, the present invention refers to a process for the preparation of a key intermediate for the preparation of sevoflurane.

The present invention describes a process for the preparation of chloromethyl 2,2,2-trifluoro-1-(trifluoromethyl)ethyl ether also known as chloromethyl 1,1,1,3,3,3-hexafluoro-2-propyl ether as well as SEVOCHLORANE. Sevochlorane is a key intermediate in various synthetic processes for sevoflurane.

Sevoflurane, whose chemical name is fluoromethyl 2,2,2-(trifluoro-1-trifluoromethyl)ethyl ether, was developed for use as an inhalation anesthetic.

The first reference, which describes the preparation of sevoflurane, is British patent GB 1,250,928, which describes the synthesis of 1,3-polyhalo-2-propyl ethers and the use of the same as anesthetics. The process employed consists of preparing the intermediate sevochlorane, by free radical chlorination of 1,1,1,3,3,3-hexafluoro-2-propyl methyl ether with gaseous chlorine and luminous irradiation. This free radical chlorination results in a very low yield, being that the practical yield in obtaining sevoflurane at the end of the process is approximately 30% of the theoretical value. Sevoflurane is obtained by the reaction of sevochlorane with potassium fluoride in tetrahydrothiophene dioxide, commercially known as sulfolane, employing heating.

The vast majority of the commercial processes preferred for the preparation of sevoflurane rely on the use of hexafluoroisopropanol (HFIP) as starting material.

There are processes described in the literature in which sevoflurane is obtained directly from hexafluoroisopropanol without involving intermediates. This is the case, for example, of the processes for the synthesis of sevoflurane described in U.S. Pat. Nos. 4,250,334 and 4,469,898.

U.S. Pat. No. 4,250,334 describes a method for the synthesis of sevoflurane, consisting of the reaction of hexafluoroisopropanol with a mixture of hydrofluoric acid, paraformaldehyde and a dehydrating agent. Although it is a "one pot" method, during the production of sevoflurane and its subsequent distillation, a large quantity of hexafluoroisopropanol is co-distilled with the product, which results in large losses of this reagent, which is also an impurity, whose removal in posterior purification steps is critical, and difficult to accomplish. In addition to this inconvenience, the formation of side products is elevated, being that the final product is obtained, in an appropriate degree of purity, only after various purifications steps by fractional distillation.

U.S. Pat. No. 4,469,898 describes the synthesis of sevoflurane from hexafluoroisopropanol, hydrofluoric acid and a desiccating agent, in special equipment where unconsumed hexafluoroisopropanol is recycled. Various desiccating agents are employed such as sulfuric, phosphoric, trifluoromethanesulfonic acids, etc. The reported yields for this process are low and the isolated product presents low purity.

Particularly useful for the preparation of sevoflurane are those processes, which first prepare the intermediate sevochlorane, followed by fluorination through a halogen exchange reaction.

U.S. Pat. No. 6,100,434 describes the synthesis of sevoflurane through the preparation of sevochlorane and subsequent fluorination of this intermediate with potassium fluoride in a high molecular weight solvent. Sevochlorane is prepared from hexafluoroisopropanol, aluminum trichloride and 1,3,5-trioxane. An excess of aluminum trichloride in the reaction medium results predominantly in the formation of 2,2'-[methylenebis(oxy)]bis-(1,1,1,3,3,3-hexafluoropropane)—hereinafter denominated P1. The reaction is interrupted by addition of a 6N HCl solution to decompose the gel of hydroxydichloroaluminate. The authors relate that the isolated product contained 95% sevochlorane, <5% of P1 and <1% of higher molecular weight polyacetals. The crude yield described was 87%. Among the disadvantages of this process is the fact that large quantities of aluminum trichloride must be handled, which is a highly hygroscopic solid and whose reaction with atmospheric humidity or with residual water present tends to be violent. The fact that this reagent easily reacts with water, resulting in the formation of acidic gasses, causes a reduction in its content, compromising considerably the yield of the reaction and the purity of the isolated product. The addition of 6N hydrochloric acid to interrupt the reaction is an additional disadvantage of the process, violently elevating the reaction temperature, resulting in partial product loss by decomposition, volatilization and polymerization. Finally, this reaction generates as a residue, an aqueous phase containing hydroxyaluminates that require incineration for disposal, incurring additional costs.

U.S. Pat. No. 6,245,949 describes the synthesis of sevoflurane by reaction of hexafluoroisopropanol with dimethoxymethane and the resulting product is submitted to reaction with aluminum trichloride and potassium fluoride. Once again there is the disadvantage of working with aluminum trichloride, which is hygroscopic and easily inactivated in the presence of humidity. The yield of the process is quite low, being declared by the author as 50%.

U.S. Pat. No. 6,271,422 describes the synthesis of sevoflurane by fluoromethylation of alcohols via decarboxylative halogenation. In this way, hexafluoroisopropanol is submitted to reaction with ethyl alpha-bromoacetate providing alpha-(hexafluoroisopropoxy)acetic acid in a yield of 66%. This intermediate is subjected to reaction with highly toxic lead tetra-acetate, using carcinogenic benzene as the solvent. In the reaction sequence, the homogeneous benzene/sevochlorane solution, which is inseparable by distillation, is reacted with potassium fluoride providing at the end of the process sevoflurane with a low yield of 28%.

U.S. Pat. No. 5,886,239 describes the synthesis of sevoflurane by reacting sevochlorane with the salt obtained from the reaction between sterically hindered tertiary amines, such as di-isopropylethylamine, and hydrofluoric acid. The process described is incomplete and results in low purity sevoflurane, which requires various purifications steps by fractional distillation to obtain a level of purity necessary for clinical use, which reduces considerably the yield declared by the inventors.

Various other references exist which describe the synthesis of sevoflurane employing uncommon reagents, or by way of processes, which are not industrially applicable due to their complexity or low yields.

The processes which involve the reaction of hexafluoroisopropanol with the formation of the intermediate sevochlorane are of particular interest, since this intermediate can be easily converted to sevoflurane through procedures well described in the literature.

Employing the processes described up to the present moment, the production of sevochlorane is problematic due to incomplete reactions with low yields, or require difficult to handle and highly toxic reagents, or yield a product containing impurities difficult to separate.

The present invention describes a novel process for the preparation of sevochlorane, which presents high yields, resulting in a product of high purity, and presenting the additional advantage of being robust in the presence of atmospheric humidity, without affecting adversely the reaction yield.

In addition to these factors, the process described in the present invention employs reagents, which are easy to handle and transport, and generates residues that are easily treated.

In accordance with the embodiments of the present invention, chloromethyl 2,2,2-trifluoro-1-(trifluoromethyl)-ethyl ether (sevochlorane) is prepared by chloromethylation of hexafluoroisopropanol (HFIP) with: a formaldehyde equivalent, such as, but not limited to, paraformaldehyde (polymerized formaldehyde $(CH_2O)_n$) or 1,3,5-trioxane (the cyclic trimer of formaldehyde); a chlorinating agent such as, but not limited to, oxalyl chloride, phosphorus trichloride, phosphorus pentachloride, phosphorus oxychloride, sulfuryl chloride or, preferably, thionyl chloride; and a strong acid such as, but not limited to, concentrated or fuming sulfuric acid.

The reaction temperature will vary according to the combination of reagents employed. Independently from what reagents are combined, the addition of the reagents may be conducted at temperatures ranging between $-35°$ C. and $20°$ C., preferably below $20°$ C. After this addition step, the reaction temperature is kept between $0°$ C. and $60°$ C., preferably between $15°$ C. and $35°$ C.

The reaction is accomplished in an equipment consisting of a flask or reactor equipped with magnetic or mechanical stirring, thermometer, addition funnel and a cooled condenser connected through a glass tube to a vessel containing a 30% sodium hydroxide solution to neutralize the HCl and $SO_2$ gasses released by the reaction.

The order of addition of the reactants, HFIP, formaldehyde equivalent, a chlorination agent such as thionyl chloride and a strong acid such as sulfuric acid, is not critical, demonstrating the flexibility of the present process. Preferably, the procedure consists of introducing the reagents HFIP, the formaldehyde equivalent and thionyl chloride to the reaction vessel. The sulfuric acid is added slowly, under stirring, maintaining the reaction temperature below $20°$ C. The procedure may, alternatively, consist of the introduction of the reagents HFIP, the formaldehyde equivalent and sulfuric acid to the reaction vessel maintaining an internal temperature below $20°$ C., thereafter; thionyl chloride is slowly added. Alternatively, the hexafluoroisopropanol may be slowly added to the reaction mixture. The reaction is kept at a temperature ranging between $15°$ C. and $35°$ C., and is characterized by the release of gasses (HCl and $SO_2$), but after a period of stirring, a separation of phases is observed.

Experiments have shown that the purity of the isolated product depends on the number of equivalents of thionyl chloride and formaldehyde employed, these reagents being preferably employed in excess in relation to HFIP. It was also observed that the use of formaldehyde in excess in relation to HFIP favors the separation of phases during the reaction, where the lower phase consists of an extremely acidic mixture, and the upper phase consists of the desired product, sevochlorane.

In a preferable embodiment of the present invention, the reaction employs 1 equivalent of HFIP, 1.5 equivalents of paraformaldehyde (calculated considering the molecular weight of formaldehyde, $CH_2O$, equal to 30), 1.8 equivalents of thionyl chloride and 1.5 equivalents of sulfuric acid in order to produce sevochlorane with a purity above 95%. Preferably, the addition of the reagents is conducted at temperatures between $0°$ C. and $20°$ C. The temperature varies at the beginning of the addition of sulfuric acid to the reaction mixture, and, due to this fact, the temperature in this step should be controlled to avoid HFIP losses and subsequent reduction in yield.

The reaction is monitored by gas chromatography (GC), where, initially, a mixture of products is formed which consists of sevochlorane and by-products. Surprisingly, the by-products, which are formed in the first few hours of the reaction, are converted to sevochlorane as the reaction progress, which, in this manner, does not affect the global yield of the desired product. This fact is contrary to the previously described processes, which also use HFIP as a raw material, wherein the formation of said by-products results in an effective reduction in chemical yield.

The by-products obtained in the present process are compounds already known and described in the preparation of sevochlorane and/or sevoflurane via other routes. The principal by-products identified in the first hours of the reaction, according to the present invention for the preparation of sevochlorane are:

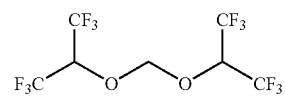

referred to hereinafter as P1

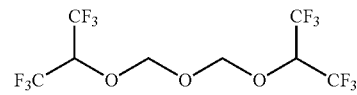

referred to hereinafter as P2

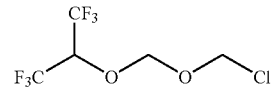

referred to hereinafter as P3

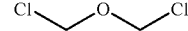

referred to hereinafter as bisCl

Interestingly, the initial formation of the by-products can be explained due to the initial reaction among paraformaldehyde, sulfuric acid and HFIP. The break of paraformaldehyde during the addition of sulfuric acid to the reaction medium explains the observed exothermic process that is controlled by keeping the temperature below $20°$ C. During the elapsing of the reaction chlorosulfonic acid is slowly formed in the reaction medium, through an endothermic reaction of sulfuric acid with thionyl chloride. The chlorosulfonic acid, generated in situ, reacts with the by-products mixture, through an exothermic reaction, with formation of the sevochlorane. In that way a thermal compensation is observed during the elapsing of the reaction allowing the same to happen in a soft way, and the product is obtained with high yield and purity, without direct contact with the corrosive chlorosulfonic acid.

Sevochlorane produced according to the process of the present invention may be isolated from the reaction medium by separation of the liquid phases of the reaction medium or, if this separation does not occur naturally, water may be added to the reaction medium keeping the temperature between 0° C. and 10° C., followed by separation of the phases.

The crude sevochlorane thus obtained may be treated with alkaline solutions in order to adjust the pH and remove undesired by-products from the reaction. Sevochlorane has a very low solubility in water, being present in the lower phase while water-soluble impurities will be present in the upper aqueous phase. Sevochlorane may be separated from the aqueous phase by conventional techniques.

According to a present invention, the product, crude sevochlorane, is treated with an alkaline solution to remove the excess of acids and to correct the pH. The alkaline solution employed may be an aqueous solution of an alkali or alkaline earth metal carbonate or hydroxide, or ammonia. Preferably, the crude sevochlorane is treated with a 10% sodium carbonate solution in sufficient quantity to result in a neutral final pH.

The product, sevochlorane, at neutral pH is then treated with an aqueous solution of an alkali or alkaline earth metal hydroxide, preferably, 10% sodium hydroxide to facilitate the decomposition and removal of residual by-products like bischloromethyl ether-bisCl. Sevochlorane may then be separated from the aqueous phase by conventional techniques.

The sevochlorane thus obtained, according to the present invention, may be converted to sevoflurane in a reaction medium containing potassium fluoride or sodium fluoride and purified by fractional distillation. The concentrated distillate, enriched in acetal $(CF_3)_2CHOCH_2OCH(CF_3)_2$ (P1) may be used as new raw material for the preparation of sevochlorane according to the processes described in the present invention, substituting HFIP as a raw material.

According to another embodiment of the present invention, the chloromethyl 2,2,2-trifluoro-1-(trifluoromethyl)ethyl ether (sevochlorane) is manufactured through the reaction of an acetal of the formula (I)

$$(CF_3)_2CHO(CH_2O)_nR \quad (I)$$

where R is a $C_1$-$C_4$ alkyl group or a haloalkyl group wherein the halogen is fluorine, chlorine or bromine, and where "n" is an integer between 1 and 10, with: a formaldehyde equivalent, such as, but not limited to, a paraformaldehyde (polymerized formaldehyde $(CH_2O)_n$) or 1,3,5-trioxane (the cyclic trimer of formaldehyde); a chlorinating agent such as, but not limited to, oxalyl chloride, phosphorus trichloride, phosphorus pentachloride, phosphorus oxychloride, sulfuryl chloride, or, preferably, thionyl chloride; and a strong acid such as, but not limited to, concentrated or fuming sulfuric acid.

The reaction temperature will vary according to the combination of reagents employed. The addition of the reagents may be conducted at temperatures ranging between −35° C. and 20° C., preferably below 20° C. After this addition step, the reaction temperature is kept between 0° C. and 60° C., preferably between 15° C. and 35° C.

The preferred acetals of formula (I) have the general formula of: $(CF_3)_2CHO(CH_2O)_mCH(CF_3)_2$, where "m" is an integer between 1 and 7.

Examples of preferred acetals include $(CF_3)_2CHOCH_2OCH(CF_3)_2$, $(CF_3)_2CHOCH_2OCH_2OCH(CF_3)_2$ or mixtures thereof.

The process for the preparation of sevochlorane according to this embodiment of present invention is particularly applicable for recovering the acetals formed as by-products in the synthesis of sevoflurane. In the present case, the acetals are a major constituent of a mixture comprising acetals, sevochlorane, sevoflurane and other by-products formed in the synthesis of sevoflurane.

The reaction is accomplished in equipment consisting of a flask or reactor equipped with magnetic or mechanical stirring, a thermometer, addition funnel and a cooled condenser connected through a glass tube to a vessel containing a 30% sodium hydroxide solution to neutralize the gasses (HCl e $SO_2$) released in the reaction.

The procedure consists of introducing an acetal of the formula (I), or a mixture enriched in acetal, a formaldehyde equivalent and a chlorinating agent such as thionyl chloride to the reaction vessel. The acid such as sulfuric acid is then added slowly, under stirring, maintaining a reaction temperature below 20° C. The procedure may, alternatively, consist of introduction of an acetal, or a mixture enriched in acetal, a formaldehyde equivalent and sulfuric acid to the reaction vessel, maintaining the internal temperature below 20° C. Thionyl chloride is then slowly added. Alternatively, the acetal or a mixture enriched in acetal may be slowly added to the reaction mixture. The reaction is kept at temperature ranging between 15° C. and 35° C., and is characterized by the liberation of gasses (HCl and $SO_2$) but, after a period of stirring, a separation of phases is observed.

As it has been verified when HFIP is used as starting material, the reaction using an acetal of the formula (I) employs 1.8 equivalents of thionyl chloride and 1.5 equivalents of sulfuric acid per equivalent of acetal, however, 0.7-1.5 equivalents of paraformaldehyde may be employed to produce sevochlorane with above 95% purity. The number of equivalents of paraformaldehyde is calculated considering the molecular weight of the monomer $CH_2O$ equal to 30.

Preferably, the addition of the reagents is conducted at temperatures between 0° C. and 20° C. and, after the addition step, the reaction is conducted at a temperature ranging between 15° C. and 35° C. The temperature varies at the beginning of the addition of sulfuric acid to the reaction mixture, and, due to this fact, the temperature in this step should be controlled to avoid regenerated HFIP losses and subsequent reduction in yield.

Also in this case, the break of paraformaldehyde during the addition of sulfuric acid to the reaction medium explains the observed exothermic process that is controlled by keeping the temperature below 20° C. During the elapsing of the reaction chlorosulfonic acid is slowly formed in the reaction medium, through an endothermic reaction of sulfuric acid with thionyl chloride. The chlorosulfonic acid, generated in situ, reacts with the acetal or a mixture of acetals, through an exothermic reaction, with formation of the sevochlorane and HFIP. The regenerated HFIP is converted in sevochlorane. In that way a thermal compensation is observed during the elapsing of the reaction allowing the same to happen in a soft way, and the product is obtained with high yield and purity, without direct contact with the corrosive chlorosulfonic acid.

The following examples are presented for illustrative purposes only, and are not intended to limit the scope of the present invention.

EXAMPLE 1

Preparation of Sevochlorane

Effect of the Quantities of Reagents on the Yield and Purity of the Product

Table 1 presents the results of a series of experiments, which were accomplished with the purpose of investigating the influence of the reagents quantities with respect to the yield and purity of the product, sevochlorane. In each of the experiments, 1 equivalent of HFIP was used and the number of equivalents of the remaining reagents were varied as shown in table 1.

TABLE 1

Influence of the quantities of reagents on the yield and purity of the product sevochlorane.

| Trial | $SOCl_2$ (eq.) | $H_2SO_4$ (eq.) | $CH_2O$* (eq.) | Sevochlorane (%) | Yield (%) |
|---|---|---|---|---|---|
| 1  | 1.2 | 1   | 1   | 65.6 | 71.8 |
| 2  | 1.7 | 1   | 1   | 98.2 | 50.0 |
| 3  | 2.2 | 1   | 1   | 99.2 | 46.4 |
| 4  | 1.2 | 1.4 | 1   | 69.8 | 72.4 |
| 5  | 1.7 | 1.4 | 1   | 98.1 | 55.1 |
| 6  | 2.2 | 1.4 | 1   | 92.7 | 26.0 |
| 7  | 1.2 | 1.8 | 1   | 78.2 | 71.2 |
| 8  | 1.7 | 1.8 | 1   | 98.1 | 54.4 |
| 9  | 2.2 | 1.8 | 1   | 90.7 | 44.0 |
| 10 | 1.2 | 1   | 1.5 | 40.5 | 71.1 |
| 11 | 1.7 | 1   | 1.5 | 90.5 | 73.9 |
| 12 | 2.2 | 1   | 1.5 | 94.8 | 61.8 |
| 13 | 1.2 | 1.4 | 1.5 | 53.7 | 69.6 |
| 14 | 1.7 | 1.4 | 1.5 | 92.5 | 76.1 |
| 15 | 2.2 | 1.4 | 1.5 | 97.6 | 55.2 |
| 16 | 1.2 | 1.8 | 1.5 | 55.2 | 75.2 |
| 17 | 1.7 | 1.8 | 1.5 | 89.4 | 76.0 |
| 18 | 2.2 | 1.8 | 1.5 | 97.4 | 45.9 |
| 19 | 1.2 | 1   | 2   | 24.4 | 75.4 |
| 20 | 1.7 | 1   | 2   | 72.1 | 73.3 |
| 21 | 2.2 | 1   | 2   | 93.2 | 66.9 |
| 22 | 1.2 | 1.4 | 2   | 23.6 | 81.0 |
| 23 | 1.7 | 1.4 | 2   | 66.4 | 84.4 |
| 24 | 2.2 | 1.4 | 2   | 92.2 | 72.4 |
| 25 | 1.2 | 1.8 | 2   | 39.7 | 75.9 |
| 26 | 1.7 | 1.8 | 2   | 73.9 | 77.0 |
| 27 | 2.2 | 1.8 | 2   | 95.0 | 75.5 |

*The formaldehyde equivalent used was paraformaldehyde.

The general procedure involves a reactor equipped with mechanical or magnetic stirring, thermometer, addition funnel and a cooled condenser, to which were added HFIP, paraformaldehyde and thionyl chloride. The condenser was connected through an U-shape glass tube to a vessel containing a 30% sodium hydroxide solution in order to neutralize the gasses generated in the reaction. Sulfuric acid was added slowly, via an addition funnel, maintaining the temperature of the reaction below 20° C. with a water/ice bath. The mixture was maintained under stirring and at a temperature between 15° C. and 35° C. for 6 hours. The stirring was stopped, and the mixture was transferred to a separation funnel and the organic phase (upper phase) was returned to the reaction flask. The mixture was cooled to approximately 0° C. and a 10% sodium carbonate solution was added via an addition funnel until the aqueous phase attained a stable pH of 7, maintaining the temperature between 0° C. and 10° C. When the separation of phases in the reaction medium was not observed, the mixture was cooled to 0° C. and water was added until a clean separation of the phases occurred. In this case, the organic phase was returned to the reaction flask, the mixture was cooled to approximately 0° C. and a 10% sodium carbonate solution was added via an addition funnel until the pH of the aqueous phase attained a pH of 7, maintaining the temperature between 0° C. and 10° C. The product, sevochlorane, was analyzed by gas chromatography.

The results presented in Table 1 show that the quantities of thionyl chloride and formaldehyde have a significant influence on the yield and purity of the product. By means of treating the analytical data with statistic tools it can be realized the following statements. To obtain a sevochlorane with high purity it is employed 1.6 to 2.2 equivalents of thionyl chloride, 1.0 to 2.0 equivalents of sulfuric acid and 1.0 to 2.0 equivalent of formaldehyde per equivalent of HFIP (trials 2, 3, 5, 6, 8, 9, 11, 12, 14, 15, 18, 21, 24, 27). To obtain a sevochlorane with high purity and yield it is employed 1.7 to 2.0 equivalents of thionyl chloride, 1.0 to 2.0 equivalents of sulfuric acid and 1.5 to 2.0 equivalent of formaldehyde per equivalent of HFIP (trials 11, 14, 24 e 27). Preferably, it is employed 1.8 equivalents of thionyl chloride, 1.5 equivalent of sulfuric acid and 1.5 equivalent of formaldehyde per equivalent of HFIP.

EXAMPLE 2

Preparation of Sevochlorane

Effect of the Order of Addition of the Reagents

Table 2 presents the results of the experiments, which were accomplished with the purpose of investigating the influence of the order of addition of the reagents on the yield and purity of the product, sevochlorane. In each of the experiments 1 equivalent of HFIP, 1.8 equivalents of thionyl chloride, 1.5 equivalents of sulfuric acid and 1.5 equivalents of formaldehyde were used.

Reaction 1 corresponds to the addition of sulfuric acid to a mixture of HFIP, paraformaldehyde and thionyl chloride, while reaction 2 corresponds to the addition of thionyl chloride to a mixture of HFIP, paraformaldehyde and sulfuric acid.

TABLE 2

Influence of the order of addition of the reagents on the process for the preparation of sevochlorane according to the present invention.

| Reaction* | Yield (%) | Temp.** | Sevochlorane (%) | P1 (%) | HFIP (%) | Other by-products (%)*** |
|---|---|---|---|---|---|---|
| 1 | 76 | 20° C. | 99 | 0.3 | 0.2 | 0.5 |
| 2 | 71 | 35° C. | 98 | 0.2 | 0.1 | 1.7 |

*6 hours of reaction.
**temperature of the mixture HFIP, paraformaldehyde and (thionyl chloride or sulfuric acid).
***By-products: bisCl, P2 and P3

The general procedure involves a reactor equipped with mechanical or magnetic stirring, thermometer, addition funnel and a cooled condenser, to which were added the HFIP, paraformaldehyde and thionyl chloride or sulfuric acid. The condenser was connected through an U-shape glass tube to a vessel containing a 30% sodium hydroxide solution to neutralize the gasses generated in the reaction. Sulfuric acid or thionyl chloride was then added slowly, via an addition funnel under stirring, maintaining the reaction temperature below 20° C. with a water/ice bath. The mixture was maintained under stirring and at a temperature between 15° C. and 35° C. for 6 hours. The mixture was then transferred to a separation funnel, and the phases were separated. The organic phase was treated with a 10% sodium carbonate solution until the pH turned basic, maintaining the temperature between 0° C. and 10° C. A 10% sodium hydroxide solution was added to this mixture which was then maintained under stirring for one hour. The product was isolated as a colorless liquid.

The results presented in Table 2 show that the order of addition of the reagents does not have a significant influence on the yield or purity of the sevochlorane obtained.

Reaction 2 showed a slight exothermic process during mixture of the HFIP and paraformaldehyde with sulfuric acid, raising the temperature of the reaction medium to 35° C. Although this behavior did not influence on the yield or purity of the product sevochlorane, the execution of the process for the preparation of sevochlorane according to the present invention preferably employs the order of addition of the reagents according to reaction 1.

EXAMPLE 3

Preparation of Sevochlorane from HFIP Under Optimized Conditions and Treatment of the Crude Sevochlorane In a reactor equipped with magnetic stirring, thermometer, addition funnel and a cooled condenser, there was added HFIP (317 mL; 3.0 mol; 1 eq.), paraformaldehyde (134 g, 4.47 mol; 1.5 eq.) and thionyl chloride (400 mL, 5.48 mol; 1.8 eq.). The condenser was connected through an U-shape glass tube to a vessel containing a 30% sodium hydroxide solution to neutralize the gasses generated in the reaction. Sulfuric acid (243 mL, 4.57 mol, 1.5 eq.) was added slowly, via an addition funnel and under stirring, maintaining the reaction temperature below 20° C. with a water/ice bath. The mixture was maintained under stirring and at a temperature between 15° C. and 35° C. for 6 hours. An aliquot of the reaction mixture was cooled and treated with water and a 10% sodium carbonate solution, and then analyzed by gas chromatography showing the following composition: 97% sevochlorane, 0.3% P1, 0.01 HFIP and 2.4% bis-chloromethyl ether, P3 and P2. The stirring was stopped, and the mixture was transferred to a separation funnel and the organic phase (upper phase) was returned to the reaction flask. The mixture was cooled to approximately 0° C. and a 10% sodium carbonate solution (620 mL) was added via an addition funnel until the aqueous phase attained a stable pH of 7, maintaining the temperature between 0° C. and 10° C. A 10% sodium hydroxide solution (544 mL) was then added. The mixture was maintained under stirring for one hour and an aliquot of the organic phase was analyzed by gas chromatography which revealed the presence of 99% sevochlorane, 0.3% P1, 0.001% HFIP, 0.40% P3 and less than 0.5% of bis-chloromethyl ether. The mixture was transferred to a separation funnel. The product (lower phase) was separated, resulting in a colorless liquid (520 g; yield: 80%). Analysis by gas chromatography of the final product showed the following composition: sevochlorane (99.3%), HFIP (0.04%), P1 (0.3%), P2 and P3 (total of 0.4%).

EXAMPLE 4

Preparation of Sevochlorane from the Acetal $(CF_3)_2CHOCH_2OCH(CF_3)_2$—(P1)—Under the Optimized Conditions for the Reaction with HFIP as Starting Material In a reactor equipped with magnetic stirring, thermometer, addition funnel and a cooled condenser, there was added P1 (348 g; 1.0 mol; 1 eq., purity greater than 98%), paraformaldehyde (45 g, 1.5 mol; 1.5 eq.) and thionyl chloride (133 mL, 1.8 mol; 1.8 eq.). The condenser was connected through an U-shape glass tube to a vessel containing a 30% sodium hydroxide solution to neutralize the gasses generated in the reaction. Sulfuric acid (81 mL, 1.5 mol, 1.5 eq.) was added slowly, via an addition funnel and under stirring, maintaining the reaction temperature below 20° C. with a water/ice bath. The mixture was maintained under stirring and at temperature between 15° C. and 35° C. for 4 hours. An aliquot of the reaction was cooled and treated with water and a 10% sodium carbonate solution, and then analyzed by gas chromatography, showing the following composition: 91% sevochlorane, 5% P1, 0.3 HFIP, 3% of bis-chloromethyl ether, P3 and P2. The mixture was maintained under stirring for 2 additional hours and another aliquot, treated in the same way, was analyzed by gas chromatography showing the following composition: 98% sevochlorane, 0.3% P1, 0.4 HFIP, 1.3% bis-chloromethyl ether, P3 and P2. The stirring was stopped, and the mixture was transferred to a separation funnel and the organic phase (upper phase) was returned to the reaction flask. The mixture was cooled to approximately 0° C. and a 10% sodium carbonate solution (200 mL) was added via an addition funnel until the aqueous phase attained a stable pH of 7, maintaining the temperature between 0° C. and 10° C. A 10% sodium hydroxide solution (180 mL) was added to the mixture which was maintained under stirring for one hour, and an aliquot of the organic phase was analyzed by gas chromatography, revealing the presence of 99% sevochlorane. The mixture was transferred to a separation funnel and the product (lower phase) was separated, resulting in a colorless liquid (315 g; yield: 73%). Analysis by gas chromatography of the final product revealed the presence of >99% sevochlorane.

EXAMPLE 5

Preparation of Sevochlorane from a Mixture of the Acetal $(CF_3)_2CHOCH_2OCH(CF_3)_2$, Sevochlorane, Sevoflurane and Other By-Products from the Synthesis of Sevoflurane Effect of the Number of Equivalents of Formaldehyde on the Yield and Purity of the Product Experiments were accomplished with the purpose of investigating the influence of the number of equivalents of formaldehyde on the yield and purity of the product sevochlorane. In each of the experiments 1 equivalent of a mixture enriched in the acetal $(CF_3)_2CHOCH_2OCH(CF_3)_2$ (calculated considering a mixture composed only by $(CF_3)_2CHOCH_2OCH(CF_3)_2$), 1.8 equivalents of thionyl chloride and 1.5 equivalents of sulfuric acid were used. A mixture enriched in the acetal $(CF_3)_2CHOCH_2OCH(CF_3)_2$ used as starting material for the synthesis of sevochlorane was analyzed by gas chromatography and showed the following composition: 46% $(CF_3)_2CHOCH_2OCH(CF_3)_2$, 28% sevoflurane, 15% sevochlorane and 11% of other by-products.

The general procedure involves a reactor equipped with mechanical or magnetic stirring, thermometer, addition funnel and a cooled condenser, to which was added a mixture enriched in the acetal $(CF_3)_2CHOCH_2OCH(CF_3)_2$, formaldehyde in the quantities described in table 3 and 1.8 equivalents of thionyl chloride. The condenser was connected through an U-shape glass tube to a vessel containing a 30% sodium hydroxide solution to neutralize the gasses generated in the reaction. Sulfuric acid (1.5 eq.) was added slowly, via an addition funnel and under stirring, maintaining the reaction temperature below 20° C. with a water/ice bath. The resulting mixture was maintained under stirring and at temperature between 15° C. and 35° C. for 6 hours. The stirring was stopped, and the mixture was transferred to a separation funnel and the organic phase (upper phase) was returned to the reaction flask. The mixture was cooled to approximately 0° C. and a 10% sodium carbonate solution (200 mL) was added via an addition funnel until the aqueous phase attained a stable pH of 7, maintaining the temperature between 0° C. and 10° C. The phases were separated and the organic phase was isolated as a colorless liquid, which was analyzed by gas chromatography.

TABLE 3

Influence of the number of equivalents of formaldehyde on the yield and purity of sevochlorane.

| Trial* | Yield (%) | CH$_2$O** (eq.) | Separation of phases | Sevochlorane (%) | P1 (%) | HFIP (%) | Other by-products (%)*** |
|---|---|---|---|---|---|---|---|
| 1 | 33 | 0 | no | 95 | 2 | 2 | 0.3 |
| 2 | 33 | 0.2 | no | 95 | 0.8 | 1.5 | 0.8 |
| 3 | 86 | 0.7 | yes | 94 | 1 | 1 | 3.3 |
| 4 | 86 | 0.81 | yes | 97 | 0.3 | 0 | 2.3 |
| 5 | 100 | 1.5 | yes | 90 | 1.3 | 0 | 8 |

*6 hours of reaction.
**Formaldehyde equivalent used is paraformaldehyde.
***Other by-products: sum of BisCl, P2 e P3

The results presented in Table 3 show that the use of 0.7-1.5 equivalents of formaldehyde in relation to the mixture enriched in the acetal (CF$_3$)$_2$CHOCH$_2$OCH(CF$_3$)$_2$ favors the yield and purity of sevochlorane.

EXAMPLE 6

Detailed Description of Trial 4 of Example 5 Including the Step of Treatment of Crude Sevochlorane In a reactor equipped with magnetic stirring, thermometer, addition funnel and a cooled condenser, it was added a mixture enriched in acetal (CF$_3$)$_2$CHOCH$_2$OCH(CF$_3$)$_2$ (100 g; 0.29 mol; 1 eq.), paraformaldehyde (7.2 g; 0.24 mol; 0.8 eq.) and thionyl chloride (38 mL; 0.5 mol; 1.8 eq.). The condenser was connected through an U-shape glass tube to a vessel containing a 30% sodium hydroxide solution to neutralize the gasses generated in the reaction. Sulfuric acid (23 mL; 0.4 mol; 1.5 eq.) was added slowly, via an addition funnel and under stirring, maintaining the reaction temperature below 20° C. with a water/ice bath. The mixture was maintained under stirring and at temperature between 15° C. and 35° C. for 4 hours. An aliquot of the reaction was cooled and treated with water, a 10% sodium carbonate solution and then analyzed by gas chromatography, showing the following composition: 83% sevochlorane, 11% P1 and 5% bis-chloromethyl ether, P3 and P2. The mixture was maintained under stirring for an additional 2 hours and another aliquot was treated and analyzed by gas chromatography showing the presence of 97% sevochlorane, 0.3% P1, 2% bis-chloromethyl ether, P3 and P2. The stirring was stopped, and the mixture was transferred to a separatory funnel and the organic phase (upper phase) was returned to the reaction flask. The mixture was cooled to approximately 0° C. and a 10% sodium carbonate solution was added via an addition funnel until the aqueous phase attained a stable pH of 7, maintaining the temperature between 0° C. and 10° C. A 10% sodium hydroxide solution was added and the mixture was maintained under stirring for one hour, and an aliquot of the organic phase was analyzed by gas chromatography, revealing the presence of 99% sevochlorane. The mixture was transferred to a separation funnel and the product (lower phase) was separated, resulting in a colorless liquid (92 g; yield: 87%). Analysis by gas chromatography of the final product revealed the presence of >99% sevochlorane.

The invention claimed is:

1. A process for the preparation of chloromethyl 2,2,2-trifluoro-1-(trifluoromethyl) ethyl ether (sevochlorane) comprising reacting hexafluoroisopropanol (HFIP) with a formaldehyde equivalent selected from the group consisting of paraformaldehyde and 1,3,5-trioxane, a chlorinating agent selected from the group consisting of oxalyl chloride, sulfuryl chloride and thionyl chloride; and concentrated or fuming sulfuric acid; wherein the reactants are combined in a way selected from the group consisting of a) adding the sulfuric acid to a mixture of HFIP, formaldehyde equivalent and chlorinating agent; and b) adding the chlorinating agent to a mixture of HFIP, formaldehyde equivalent and sulfuric acid; and c) adding the HFIP to a mixture of the formaldehyde equivalent, sulfuric acid and chlorinating agent, thereby generating chlorosulfonic acid in situ and chloromethylating HFIP in the same pot to form sevochlorane.

2. The process according to claim 1, characterized by the fact that the formaldehyde equivalent is paraformaldehyde and the chlorinating agent is thionyl chloride.

3. The process according to claim 2, characterized by the fact that the reaction employs 1.6 to 2.0 molar equivalents of thionyl chloride, 1.0 to 2.0 molar equivalents of sulfuric acid and 1.0 to 2.0 molar equivalents of paraformaldehyde per molar equivalent of hexafluoroisopropanol.

4. The process according to claim 3, characterized by the fact that the reaction employs 1.8 molar equivalents of thionyl chloride, 1.5 molar equivalents of sulfuric acid and 1.5 molar equivalents of paraformaldehyde per molar equivalent of hexafluoroisopropanol.

5. The process according to claim 1, characterized by the fact that the reaction is conducted at a temperature between 0° C. and 60° C.

6. The process according to claim 1, comprising an additional step of treating the sevochlorane with a first aqueous alkaline solution of an alkali or alkaline earth metal carbonate or hydroxide, or with ammonia to neutralize the sevochlorane.

7. The process according to claim 6, characterized by the fact that the aqueous alkaline solution is a sodium carbonate solution.

8. The process according to claim 6, comprising an additional step of treating the neutral sevochlorane with a second aqueous alkaline solution of an alkali or alkaline earth metal hydroxide to remove reaction by-products.

9. The process according to claim 8, characterized by the fact that the second aqueous alkaline solution is a sodium hydroxide solution.

10. A process for the preparation of chloromethyl 2,2,2-trifluoro-1-(trifluoromethyl)-ethyl ether (sevochlorane) comprising reacting an acetal of the general formula (I),

(I)

where R is an alkyl or haloalkyl group wherein the halogen is fluorine, chlorine or bromine, and n is an integer between 1 and 10, with a formaldehyde equivalent selected from the group consisting of paraformaldehyde and 1,3,5-trioxane, a chlorinating agent selected from the group consisting of oxalyl chloride, sulfuryl chloride and thionyl chloride, and concentrated or fuming sulfuric acid; wherein the reactants are combined in a way selected from the group consisting of a) adding the sulfuric acid to a mixture of acetal of the formula (I), formaldehyde equivalent and chlorinating agent; b) adding the chlorinating agent to a mixture of acetal of the formula (I), formaldehyde equivalent and sulfuric acid; and c) adding the acetal of the formula (I) to a mixture of the formaldehyde equivalent, sulfuric acid and chlorinating agent; thereby generating chlorosulfonic acid in situ and chloromethylating acetal of the formula (I) in the same pot to form sevochlorane.

11. The process according to claim 10, characterized by the fact that the acetal of formula (I) is a pure isolated acetal, or a mixture of acetals.

12. The process according to claim 10, characterized by the fact that the acetal of formula (I) is the major constituent of a mixture comprising acetals, sevochlorane, sevoflurane and other by-products of the synthesis of sevoflurane.

13. The process according to claim 10, characterized by the fact that the acetal of formula (I) is $(CF_3)_2CHO(CH_2O)_mCH(CF_3)_2$ where m is an integer between 1 and 7.

14. The process according to claim 10, characterized by the fact that the acetal of formula (I) is $(CF_3)_2CHOCH_2OCH(CF_3)_2$.

15. The process according to claim 10, characterized by the fact that the formaldehyde equivalent is paraformaldehyde and the chlorinating agent is thionyl chloride.

16. The process according to claim 15, characterized by the fact that the reaction employs 1.6 to 2.0 molar equivalents of thionyl chloride, 1.0 to 2.0 molar equivalents of sulfuric acid and 0.7 to 2.0 molar equivalents of paraformaldehyde per molar equivalent of acetal.

17. The process according to claim 16, characterized by the fact that the reaction employs 1.8 molar equivalents of thionyl chloride, 1.5 molar equivalents of sulfuric acid and 1.5 molar equivalent of paraformaldehyde per molar equivalent of acetal.

18. The process according to claim 10, characterized by the fact that the reaction is conducted at a temperature between 0° C. and 60° C.

19. The process according to claim 10, comprising an additional step of treating the sevochlorane with a first aqueous alkaline solution of an alkali or alkaline earth metal carbonate or hydroxide, or with ammonia, to neutralize the sevochlorane.

20. The process according to claim 19, characterized by the fact that the first aqueous alkaline solution is a sodium carbonate solution.

21. The process according to claim 19, comprising an additional step of treating the neutral sevochlorane with a second aqueous alkaline solution of an alkali or alkaline earth metal hydroxide to remove by-products.

22. The process according to claim 21, characterized by the fact that the second aqueous alkaline solution is a sodium hydroxide solution.

23. A process for the preparation of chloromethyl 2,2,2-trifluoro-1-(trifluoromethyl)-ethyl ether (sevochlorane) comprising:
  (i) adding the reactants acetal or hexafluoroisopropanol (HFIP), 1.5 molar equivalents of paraformaldehyde and 1.8 molar equivalents of thionyl chloride per molar equivalent of HFIP to a reaction vessel;
  (ii) adding 1.5 molar equivalents of sulfuric acid per molar equivalent of acetal or HFIP, under stirring, maintaining the reaction temperature below 20° C.;
  (iii) maintaining the reaction mixture under stirring at a temperature ranging between 0° C. and 60° C., whereby an organic phase comprising sevochlorane is formed;
  (iv) separating the resulting upper organic phase comprising sevochlorane; treating the organic phase comprising sevochlorane with a 10% aqueous sodium carbonate solution until the aqueous phase attains a pH of 7 indicating a neutral sevochlorane, while maintaining the temperature between 0° C. and 10° C.;
  (v) adding to the mixture of step (v) a 10% aqueous sodium hydroxide while maintaining the resulting mixture under stirring to obtain a highly pure sevochlorane;
  (vi) isolating the highly pure sevochlorane as a colorless liquid.

24. The process according to claim 23 wherein step (iii) is performed at a temperature between 15° C. and 35° C.

* * * * *

UNITED STATES PATENT AND TRADEMARK OFFICE
CERTIFICATE OF CORRECTION

| | | |
|---|---|---|
| PATENT NO. | : 8,039,678 B2 | Page 1 of 1 |
| APPLICATION NO. | : 12/443438 | |
| DATED | : October 18, 2011 | |
| INVENTOR(S) | : Ogari Pacheco et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 196 days.

~~This patent is subject to a terminal disclaimer.~~

Signed and Sealed this
Tenth Day of January, 2012

David J. Kappos
*Director of the United States Patent and Trademark Office*